United States Patent [19]

Richard et al.

[11] Patent Number: 5,858,937
[45] Date of Patent: Jan. 12, 1999

[54] TREATMENT OF CONTACT LENSES WITH AQUEOUS SOLUTION INCLUDING PHOSPHONIC COMPOUNDS

[75] Inventors: Wanda G. Richard, Philipsburg, N.J.; David J. Heiler, Avon, N.Y.

[73] Assignee: Bausch & Lomb Incorporated, Rochester, N.Y.

[21] Appl. No.: 795,116

[22] Filed: Feb. 6, 1997

Related U.S. Application Data

[60] Provisional application No. 60/013,304, Feb. 28, 1996, and provisional application No. 60/033,183, Dec. 17, 1996.

[51] Int. Cl.⁶ .................................. C11D 3/48; A61L 2/18
[52] U.S. Cl. ........................... 510/112; 510/383; 510/436
[58] Field of Search ................................... 510/112, 383, 510/436

[56] References Cited

U.S. PATENT DOCUMENTS

| | | | |
|---|---|---|---|
| Re. 32,672 | 5/1988 | Huth et al. .................................. 252/95 |
| 3,671,644 | 6/1972 | Irani et al. ................................ 424/346 |
| 4,528,110 | 7/1985 | Bragulla .................................. 510/383 |
| 4,614,549 | 9/1986 | Ogunbiyi et al. ........................... 134/19 |
| 4,758,595 | 7/1988 | Ogunbiyi et al. ......................... 514/635 |
| 4,812,173 | 3/1989 | Tsao et al. ................................. 134/27 |
| 5,096,607 | 3/1992 | Mowrey-McKee et al. ............ 252/106 |

FOREIGN PATENT DOCUMENTS

| | | | |
|---|---|---|---|
| 0289463 | 11/1988 | European Pat. Off. ...... C01B 15/037 |
| 94/15649 | 7/1994 | WIPO ............................... A61L 2/18 |

OTHER PUBLICATIONS

Patent Abstracts of Japan, vol. 012, No. 082 (C–481), 15 Mar. 1988 & JP 62215517A (Sunstar Inc), 22 Sep. 1987, see abstract.

*Primary Examiner*—Jerry D. Johnson
*Attorney, Agent, or Firm*—Chris P. Konkol

[57] ABSTRACT

The present invention provides non-oxidative methods for treating contact lenses and compositions for the same. The present invention includes contacting a lens with an aqueous solution comprising a phosphonic acid compound. In preferred embodiments of the invention, the subject phosphonic compounds are used in combination with antimicrobial agents for providing simultaneous disinfection and cleaning of contact lenses including the prevention or removal of protein deposits.

20 Claims, No Drawings

TREATMENT OF CONTACT LENSES WITH AQUEOUS SOLUTION INCLUDING PHOSPHONIC COMPOUNDS

This application claims the benefit of U.S. provisional application Ser. No. 60/013,304 filed on Feb. 28, 1996, and 60/033,183 filed on Dec. 17, 1996.

FIELD OF THE INVENTION

The present invention is directed toward methods for treating contact lenses and compositions for the same. The subject invention includes the use of an aqueous solution including certain phosphonic compounds. Preferred embodiments of the invention include methods and compositions for simultaneously cleaning and disinfecting contact lenses.

BACKGROUND

Generally, contact lenses in wide use fall into three categories: (1) hard lenses formed from materials prepared by polymerization of acrylic esters, such as polymethyl methacrylate (PMMA), (2) rigid gas permeable (RGP) lenses formed from silicone acrylates and fluorosilicone methacrylates, and (3) gel, hydrogel or soft type lenses made of polymerized hydrophilic or hydrophobic monomers, such as 2-hydroxyethyl methacrylate (HEMA). The hard acrylic type contact lenses are characterized by low water vapor diffusion constants, resistance to the effects of light, oxygen and hydrolysis and absorb only minor amounts of aqueous fluids.

In the normal course of wearing contact lenses, tear film and debris consisting of proteinaceous, oily, sebaceous, and related organic matter have a tendency to deposit and build up on lens surfaces. Many factors influence deposit formation, including patient to patient variation, lens material, care regimen, and environment. In general, high water, ionic lens materials absorb more protein than low water or non-ionic lens materials. As part of the routine care regimen, contact lenses must be cleaned to remove these tear film deposits and debris. If these deposits are not properly removed, both the wettability and optical clarity of the lenses are substantially reduced causing discomfort for the wearer.

Conventionally, the cleaning of contact lenses is accomplished with one or both of two general classes of cleaners. Surfactant cleaners, generally known as "daily cleaners" because of their recommended daily use, are effective for the removal of most carbohydrate and lipid derived matter. However, they are not as effective for the removal of proteinaceous matter such as lysozyme. Typically, proteolytic enzymes derived from plant, animal, and microbial sources are used to remove the more tenacious proteinaceous deposits. These "enzyme" cleaners are typically recommended for weekly use and are commonly employed by dissolving enzyme tablets in suitable aqueous solutions.

Further, contact lenses must be disinfected to kill harmful microorganisms that may be present or grow on the lenses. A number of methods for disinfecting contact lenses have been used such as contacting the lenses with a solution containing an oxidative chemical (e.g. hydrogen peroxide) or an antimicrobial agent at ambient temperatures. Alternatively, disinfection may be accomplished by exposing the lenses to elevated temperatures for specified periods of time. This latter disinfection technique requires the use of a common electrical disinfecting apparatus.

A conventional process of cleaning and disinfecting contact lenses, particularly soft contact lenses, typically involves initial steps comprising the cleaning phase wherein the lenses are rubbed with a daily cleaner to remove debris and then soaked in an enzyme cleaning solution at ambient temperature conditions, i.e., soaking for a period of at least 15 minutes, to achieve effective removal of proteinaceous deposits. In this process, after the cleaning phase, it is necessary to subsequently disinfect the lenses.

Methods have been developed which can remove proteinaceous material from contact lenses while simultaneously disinfecting the lenses. For example, U.S. Pat. No. 4,614,549 discloses a single-step method of cleaning and disinfecting contact lenses in aqueous solutions of proteolytic enzymes at temperatures of between 60° C. and 100° C. Unfortunately, this method requires the use of an electrical disinfecting apparatus and elevated temperatures. Another example of a method for simultaneously cleaning and disinfecting contact lenses is described in U.S. Pat. No. Re. 32,672 which discloses a method wherein lenses are immersed in a solution containing peroxide and a peroxide active enzyme. However, this method requires an additional step for neutralization of the residual peroxide prior to inserting the lens into the eye.

In an effort to provide greater convenience, new regimens have been developed. For example, U.S. Pat. No. 5,096,607 issued Mar. 17, 1992 discloses a cleaning and disinfection system wherein lenses are simultaneous cleaned and disinfected by immersing the lens in a multi-purpose solution in the presence of an enzymatic tablet under certain conditions of osmolality. This system provides the benefit of a single "daily" cleaning and disinfection solution that may be simultaneously employed in combination with an enzymatic cleaner, thus reducing the number of steps required for effective lens cleaning and disinfection.

Although the latter patent represents a very significant improvement in cleaning lenses that is more convenient than previous systems, further convenience is sought. More specifically, it would be desirable to provide a cleaning system that employs only a single solution, without the general need for a supplemental enzymatic cleaning agent, which cleaning system is capable of providing cleaning comparable with systems which utilize enzymatic cleaners.

SUMMARY OF THE INVENTION

The present invention includes non-oxidative methods for treating contact lenses and compositions for the same. The present invention includes contacting a lens with an aqueous solution comprising a phosphonic acid, or a physiologically compatible salt thereof, represented by the formula:

wherein Z is a connecting radical equal in valence to n, where n is 1 to 6, preferably containing 1 to 12 carbon atoms. The Z radical can include such radicals as substituted or unsubstituted saturated hydrocarbon radicals or amine-containing radicals. By "substituted or unsubstituted" is meant unsubstituted or substituted with halogen, hydroxy, amine, carboxyl, alkylcarbonyl, alkoxycarbonyl, or substituted or unsubstituted phenyl, where the substituents on the phenyl may be halogen, hydroxy, amine, carboxy, alkylcarbonyl, or alkyl, wherein said alkyl or alkoxy groups have 1 to 4 carbon atoms.

The method of the present invention comprises cleaning a contact lens with an aqueous solution comprising at least 0.003 percent weight by volume of the subject phosphonic acid, preferably 0.005 to 1.0 percent weight by volume of a subject compound, more preferably 0.01 to 0.25 percent weight by volume.

In a preferred embodiment, the subject phosphonic acid compounds may be used in combination with antimicrobial agents for providing simultaneous disinfection and cleaning of contact lenses. In a further preferred embodiment of the present invention, the subject lens-care solution provides a complete non-oxidative cleaning regimen for contact lenses, without requiring any other solutions or supplemental enzymatic cleaning agent. The cleaning regimen provides protein removal comparable to other cleaning regimens that include the use of an enzymatic cleaning agent. As such, the present invention offers significant advantages over known cleaning and disinfecting regimens.

DETAILED DESCRIPTION OF THE INVENTION

The present invention can be used with all contact lenses such as conventional hard, soft, rigid and soft gas permeable, and silicone (including both hydrogel and non-hydrogel) lenses, but is preferably employed with soft lenses. Such lenses are commonly prepared from monomers such as hydroxyethyl methacrylate, hydroxyethylmethyl methacrylate, vinylpyrrolidone, glycerolmethacrylate, methacrylic acid or acid esters and the like. Such lenses absorb significant amounts of water, which amounts range from about 4 to about 80 percent by weight.

As previously indicated, the present invention includes an aqueous solution comprising a phosphonic acid, or its physiologically compatible salt, that is represented by the following Formula (I):

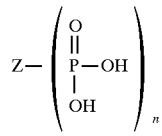
(I)

wherein Z is a connecting radical equal in valence to n, wherein n is an integer from 1 to 6, preferably 1 to 3, and preferably containing 1 to 12 carbon atoms, more preferably 1 to 10 carbon atoms. The Z radical comprises substituted or unsubstituted saturated hydrocarbon radicals or amine-containing radicals, which amine-containing radicals are saturated hydrocarbon radicals in which the carbon atoms are interrupted with at least one nitrogen atom, preferably 1 to 3 nitrogen atoms, that forms a secondary or tertiary amine. When Z is an amine-containing radical comprising one or more secondary or tertiary amines, the number of carbon atoms in Z is at least n+1. By "hydrocarbon" is meant branched, unbranched, acyclic or cyclic moieties consisting of carbon and hydrogen atoms. By "substituted or unsubstituted" is meant unsubstituted or substituted with halogen, hydroxy, amine, carboxy, alkylcarbonyl, alkoxycarbonyl or substituted or unsubstituted phenyl, where the substituents on the phenyl may be halogen, hydroxy, amine, carboxy, alkylcarbonyl, or alkyl, wherein said alkyl or alkoxy groups have 1 to 4 carbon atoms. A preferred halogen is chlorine. Preferred substituents are amine, hydroxy and substituted or unsubstituted phenyl.

Accordingly, suitable Z radicals include substituted or unsubstituted alkylidene, substituted or unsubstituted alkylene, amino tri(alkylene) having at least n+1 carbon atoms, amino di(alkylene) having at least n+1 carbon atoms, alkylenediaminetetra(alkylene) or a dialkylenetriamine penta(alkylene) radical, wherein each alkylene group in parenthesis is connected to a phosphonic acid group. Preferably, all alkylene groups independently have 1 to 4 carbon atoms.

Exemplary compounds in which the Z group is an amino tri(alkylene) radical includes amino tri(ethylidene phosphonic acid), amino tri(isopropylidene phosphonic acid), amino di(methylene phosphonic acid) mono(isopropylidene phosphonic acid), and amino mono(methylene phosphonic acid) di(ethylidene phosphonic acid). Exemplary compounds in which the Z group is a substituted or unsubstituted alkylidene radical includes methylene diphosphonic acid, ethylidine diphosphonic acid, 1-hydroxy propylidene diphosphonic acid. Exemplary compounds in which the Z group is an alkylenediaminetetra(alkylene) or a dialkylenetriamine penta(alkylene) radical include hexamethylenediaminetetra (methylene phosphonic acid) and diethylenetriaminepenta (methylenephosphonic acid).

The compounds of the present invention are either commercially available or may be prepared by various means known to the skilled artisan, including the methods disclosed in U.S. Pat. No. 3,671,644. Halo-substituted phosphonic acid compounds may be made from the corresponding hydroxy-substituted phosphonic acid compounds by employing, for example, $PCl_3$ or $PBr_3$, as will be understood by the skilled artisan.

The solutions according to the present invention are physiologically compatible. Specifically, the solution must be "ophthalmically safe" for use with a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO standards and U.S. FDA (Food & Drug Administration) regulations. The solution should be sterile in that the absence of microbial contaminants in the product prior to release must be statistically demonstrated to the degree necessary for such products.

The aqueous solution according to the present invention preferably comprises a phosphonic acid, or its physiologically compatible salt, within Formula (I) that is represented by the following Formula (II):

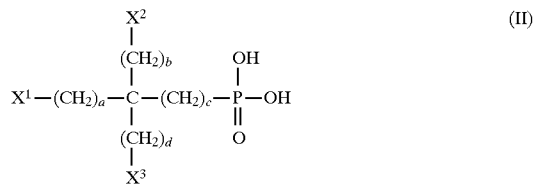
(II)

wherein each of a, b, c, and d are independently selected from integers from 0 to 4, preferably 0 or 1; $X^1$ is a phosphonic acid group (i.e., $P(OH)_2O$), hydroxy (OH), amine ($NH_2$) or hydrogen (H); and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. Preferably, the aforementioned alkyl and alkoxy groups have 1 to 4 carbon atoms, more preferably 1 carbon atom. As mentioned above, the total number of carbon atoms in Formula (II) is preferably 1 to 12, more preferably 1 to 10.

Another preferred class of compounds for use in the solutions according to the present invention comprise compounds, and physiologically compatible salts thereof, within Formula (II) that is represented by the following Formula (III):

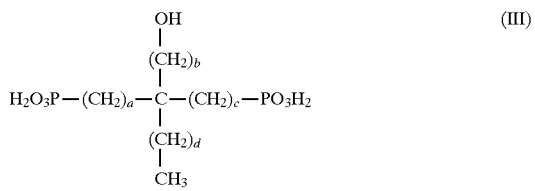

wherein each of a, b, c and d are independently selected from the integers from 0 to 4. Again, the total number of carbon atoms in Formula (III) is preferably 1 to 12, more preferably 1 to 10. (In other words, the sum of a+b+c+d in Formula (III) is preferably 1 to 11, more preferably 2 to 9).

A particularly preferred species is that wherein a, b, c, and d in Formula (II) are all 0, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

Organic phosphonic acids and their salts (collectively referred to as "phosphonic acid compounds") are generally well known in the art. The salts are sometimes referred to as phosphonates. Known uses of such phosphonic acid compounds include the inhibition of scale formation in boilers. Other known uses include the stabilization of hydrogen peroxide solutions. For example, U.S. Pat. No. 4,812,173 to Tsao et al. discloses the use of phosphonic acid compounds for stabilizing hydrogen peroxide solutions employed for disinfecting contact lenses. This method is an example of an "oxidative" disinfection which requires subsequent neutralization. Examples of oxidative disinfection are disinfecting methods employing peroxides. This reference addresses neither general "cleaning" nor removal of protein from contact lenses. Other known uses of such phosphonic compounds include their use as potentiating agents in antiseptic compositions including phenolic or quaternary ammonium bactericides. Such compositions find application in drilling mud compositions, cosmetic compositions (e.g., mouthwash, hand and hair cleaners) and heavy duty antiseptic detergent compositions (as used in commercial laundries, laundering textiles, dairy equipment, hospital equipment, etc.).

The subject aqueous solution suitably includes at least 0.003 percent weight by volume of the subject phosphonic compound in the total solution, preferably 0.005 to 1.0 percent weight by volume and more preferably about 0.01 to 0.25 percent weight by volume in the total solution.

The subject aqueous solution may also contain various other components including, but not limited to: antimicrobial agents, buffering agents, chelating and/or sequestering agents, tonicity adjusting agents, and surfactants.

The present solution comprises at least one surfactant. Suitable surfactants can be either amphoteric, cationic, anionic, or nonionic which may be present (individually or in combination) in amounts up to 15 percent, preferably up to 5 percent weight by volume (w/v) of the total composition (solution). Preferred surfactants are amphoteric or nonionic surfactants, which when used impart cleaning and conditioning properties. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available under the trademark Tween® 20), polyoxyethylene (23) lauryl ether (Brij® 35), polyoxyethyene (40) stearate (Myrj® 52), polyoxyethylene (25) propylene glycol stearate (Atlas® G 2612). One non-ionic surfactant in particular consisting of a poly(oxypropylene)-poly(oxyethylene) adduct of ethylene diamine having a molecular weight from about 7,500 to about 27,000 wherein at least 40 weight percent of said adduct is poly(oxyethylene) has been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is poloxamine. Such surfactants are available from BASF Wyandotte Corp., Wyandotte, Mich., under the registered trademark "Tetronic". An analogous of series of surfactants, suitable for use in the present invention, is the poloxamer series which is a poly(oxyethylene) poly(oxypropylene) block polymers available under the trademark "Pluronic" (commercially available form BASF).

Various other ionic as well as amphoteric and anionic surfactants suitable for in the invention can be readily ascertained, in view of the foregoing description, from *McCutcheon's Detergents and Emulsifiers*, North American Edition, McCutcheon Division, MC Publishing Co., Glen Rock, N.J. 07452 and the *CTFA International Cosmetic Ingredient Handbook*, Published by The Cosmetic, Toiletry, and Fragrance Association, Washington, D.C.

Amphoteric surfactants suitable for use in a composition according to the present invention include materials of the type are offered commercially under the trade name "Miranol." Another useful class of amphoteric surfactants is exemplified by cocoamidopropyl betaine, commercially available from various sources.

The foregoing surfactants will generally be present in a total amount from 0.01 to 5.0 percent weight by volume (w/v), preferably 0.1 to 5.0 percent, and most preferably 0.1 to 1.5 percent.

The pH of the present solutions should be maintained within the range of 5.0 to 8.0, more preferably about 6.0 to 8.0, most preferably about 6.5 to 7.8, suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred, particularly for enhancing the efficacy of biguanides. Generally, buffers will be used in amounts ranging from about 0.05 to 2.5 percent by weight, and preferably, from 0.1 to 1.5 percent. The disinfecting/preserving solutions of this invention preferably contain a borate or mixed phosphate buffer, containing one or more of boric acid, sodium borate, potassium tetraborate, potassium metaborate or mixtures of the same. In addition to buffering agents, in some instances it may be desirable to include sequestering agents in the present solutions in order to bind metal ions which might otherwise react with the lens and/or protein deposits and collect on the lens. Ethylenediaminetetraacetic acid (EDTA) and its salts (disodium) are preferred examples. They are usually added in amounts ranging from about 0.01 to about 0.3 weight percent. Other suitable sequestering agents include gluconic acid, citric acid, tartaric acid and their salts, e.g. sodium salts.

Typically, the aqueous solutions of the present invention for treating contact lenses are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Examples of suitable tonicity adjusting agents include, but are not limited to: sodium and potassium chloride, dextrose, glycerin, calcium and magnesium chloride. These agents are typically used individually in amounts ranging from about 0.01 to 2.5 % (w/v) and preferably, form about 0.2 to about 1.5% (w/v). Preferably, the tonicity agent will be employed in an amount to provide a final osmotic value of 200 to 450 mOsm/kg and more preferably between about 250 to about 350 mOsm/kg, and most preferably between about 280 to about 320 mOsm/Kg.

It may also be desirable to include water-soluble viscosity builders in the solutions of the present invention. Because of their demulcent effect, viscosity builders have a tendency to enhance the lens wearer's comfort by means of a film on the lens surface cushioning impact against the eye. Included among the water-soluble viscosity builders are the cellulose polymers like hydroxyethyl or hydroxypropyl cellulose, carboxymethyl cellulose and the like. Such viscosity builders may be employed in amounts ranging from about 0.01 to about 4.0 weight percent or less. The present solutions may also include optional demulcents.

The subject solution preferably includes at least one antimicrobial agent. As used herein, antimicrobial agents are defined as non-oxidative organic chemicals which derive their antimicrobial activity through a chemical or physiochemical interaction with the microbial organisms. Preferred antimicrobials are the quaternary ammonium compounds and biguanides.

Representative examples of the quaternary ammonium compounds are compositions comprised of benzalkonium halides or, for example, balanced mixtures of n-alkyl dimethyl benzyl ammonium chlorides. Other examples include polymeric quaternary ammonium salts used in ophthalmic applications such as poly[(dimethyliminio)-2-butene-1,4-diyl chloride], [4-tris(2-hydroxyethyl)ammonio]-2-butenyl-w-[tris(2-hydroxyethyl)ammonio]dichloride (chemical registry number 75345-27-6) generally available as polyquaternium 1 ® from ONYX Corporation.

Representative biguanides are the bis(biguanides), such as alexidine or chlorhexidine or salts thereof, and polymeric biguanides such as polymeric hexamethylene biguanides (PHMB).

Polymeric hexamethylene biguanides (commercially available from Zeneca, Wilmington, Del.), their polymers and water-soluble salts being most preferred. Generally, the hexamethylene biguanide polymers, also referred to as polyaminopropyl biguanide (PAPB), have molecular weights of up to about 100,000. Such compounds are known and are disclosed in US Patent No. 4,758,595 which patent is incorporated herein be reference.

A disinfecting amount of antimicrobial agent is an amount which will at least partially reduce the microorganism population in the formulations employed. Preferably, a disinfecting amount is that which will reduce the microbial burden by two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test—July, 1985 Contact Lens Solution Draft Guidelines). Typically, such agents are present in concentrations ranging from about 0.00001 to about 0.5% (w/v), and more preferably, from about 0.00003 to about 0.5% (w/v).

A second disinfectant/germicide can be employed as a solution preservative, but it may also function to potentiate, compliment or broaden the spectrum of microbiocidal activity of another germicide. This includes microbiocidally effective amounts of germicides which are compatible with and do not precipitate in the solution, in concentrations ranging from about 0.00001 to about 0.5 weight percent, and more preferably, from about 0.0001 to about 0.1 weight percent. Suitable complementary germicidal agents include, but are not limited to thimerosal or other phenylmercuric salts, sorbic acid, alkyl triethanolamines, and mixtures thereof The acid-addition salts of the germicides used in the present composition may be derived from an inorganic or organic acid. In most circumstances it is preferable that the salts be derived from an acid which is readily water soluble and which affords an anion which is suitable for human usage, for example a pharmaceutically-acceptable anion. Examples of such acids are hydrochloric, hydrobromic, phosphoric, sulphuric, acetic, D-gluconic, 2-pyrrolidino-5-carboxylic, methanesulphonic, carbonic, lactic and glutamic acids. The hydrochloride salt is preferred.

In the present application, the amount of the germicide or other components in a solution according to the present invention refers to the amount formulated and introduced into the solution at the time the solution is made.

The solutions of the present invention may be formulated into specific contact lens care products, such as wetting solutions, soaking solutions, cleaning and conditioning solutions, as well as purpose type lens care solutions, etc. and mixtures thereof.

Preferably, the invention is formulated as a "multipurpose solution," meaning that the solution may be used for cleaning, chemical disinfection, storing, and rinsing a contact lens. Such solutions may be part of a "multi-purpose solution system" or "multi-purpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis. By the term "cleaning" is meant that the solution contains one or more cleaning agents in sufficient concentrations to loosen and remove loosely held lens deposits and other contaminants on the surface of a contact lens, especially if used in conjunction with digital manipulation (for example, manual rubbing of the lens with a solution) or with an accessory device that agitates the solution in contact with the lens, for example, a mechanical cleaning aid. The critical micelle concentration of a surfactant-containing solution is one way to evaluate its cleaning effectiveness.

A multi-purpose solution preferably has a viscosity of less than 75 cps, preferably 1 to 50 cps, and most preferably 1 to 25 cps and is preferably is at least 95 percent weight by volume water in the total composition.

As stated, contact lenses are cleaned by contacting the lens with the subject aqueous solution. Although this may be accomplished by simply soaking a lens in the subject solution, greater cleaning can be achieved if a few drops of the solution are initially placed on each side of the lens, and the lens is rubbed for a period of time, for example, approximately 20 seconds. The lens can then be subsequently immersed within several milliliters of the subject solution. Preferably, the lens is permitted to soak in the solution for at least four hours. Furthermore, the lens is preferably rinsed with fresh solution after the rubbing step and again after being immersed within the solution. If the subject solution includes an antimicrobial agent, the subject solution not only cleans the lens, but also disinfects. However, it will be appreciated that other "non-chemical" disinfection means may be used, e.g. heat disinfection.

Although not generally necessary, enzymatic cleaners may also be used with the subject solution treating contact lenses, especially for patients susceptible to high levels of protein deposits. If used, enzymatic tablets may be placed directly within the subject solution, is a manner like that described in U.S. Pat. No. 5,096,607.

In a first embodiment of a method according to the present invention, the method comprises cleaning a contact lens with an aqueous solution comprising 0.005 to 1.0 percent by weight of at least one phosphonic acid compound, or its physiologically compatible salt, having 1 to 12, preferably 1 to 10 carbon atoms. The carbon atoms may be in the form of a substituted or unsubstituted branched or unbranched aliphatic, cyclic aliphatic, or aromatic groups or combinations thereof Exemplary phosphonic acid compounds are those according to Formula (I) above, preferably Formula (II) above, most preferably Formula (III) above. Preferably the phosphonic acid compound has 1 or 2 phosphonic acid groups which may be in salt form.

Without wishing to be bound by theory, the phosphonic acid groups in the present compounds are believed to attach to protein molecules and loosen them from the lens material, which attachment may or may not proceed via an intermediate interaction with calcium or other ions present in the vicinity.

Preferably, the present method comprises rubbing a lens with a multi-purpose solution according the present invention, followed by soaking in the solution for a total period of time that is within a range of 10 minutes to 4 hours, prior to direct placement of the lens in the eye. By the term "direct placement" is herein meant that the solution is not diluted or rinsed off the lens with a different contact-lens solution prior to "insertion" or placement on the eye.

In yet another embodiment of a method according to the present invention, the claimed solution may be used to clean a frequent replacement lens (FRL) that is planned for replacement after not more than about three months of use in the eye, or that is planned for replacement after not more than about 30 days of use in the eye, or that is planned for replacement after not more than about two weeks in the eye. Preferably, the lens is made from a polymer comprising about 0.0 to 5 mole percent repeat units derived from methacrylic acid (MAA), 10 to 99 mole percent of repeat units derived from hydroxyethyl methacrylate, and about 0.5 to 5 mole percent of cross-linking repeat units. Cross-linking repeat units may be derived, for example, from such monomers as ethyleneglycol dimethacrylate, divinylbenzene, and trimethylpropane trimethacrylate.

Separately from, or supplementally to, immersing a contact lens in a contact-lens solution according to the present invention while the contact lens is outside the eye, the accumulation of proteins on hydrophilic contact lens can be further prevented by applying such a solution as eye drops. Thus, a opthalmologically safe solution comprising the claimed compound can be packaged in a container adapted for applying the solution as drops to the eye.

As an illustration of the present invention, several examples are provided below. These examples serve only to further illustrate aspects of the invention and should not be construed as limiting the invention.

EXAMPLE 1

An example of a preferred formulation of the subject invention is provided below in Table I. This solution was prepared by weighing out the necessary amount of the tetrasodium salt of 1-hydroxyethylidene-1,1-diphosphonic acid (also referred to as tetrasodium etidronate), commercially available as DeQuest ® 2016 from Monsanto (St. Louis, Mo.) into a glass beaker, followed by bringing the solution up to total volume with ReNu ® Multi-Purpose Solution. The pH of the resulting solution was between about 7.1 to 7.3. (If necessary, the pH of the solution may be adjusted by use of an appropriate amount of hydrochloric acid or sodium hydroxide, as indicated in Table I). The final product had the composition shown in Table I below.

TABLE I

| Constituent | % Weight by Volume |
| --- | --- |
| Polyhexamethylenebiguanide HCl (as a 20% w/w solution available under the mark Cosmocil CQ, from ICI Chemical Co.) | 0.00047 |
| Boric Acid | 0.64 |
| Sodium Borate | 0.12 |
| Edetate Disodium | 0.11 |
| Sodium Chloride | 0.49 |
| Poloxamine (Tetronic ® 1107 from BASF Co.) | 1.00 |
| Tetrasodium Etidronate (as a 30% (w/w) solution available under the mark DeQuest ® 2016 from Monsanto Co.) | |
| Hydrochloride Acid, 1N | as required for pH adjustment |
| Sodium Hydroxide, 1N | as required for pH adjustment |
| Purified Water | Balance to 100 |

EXAMPLE 2

In order to further illustrate the subject invention, a number of soft hydrogel lenses (FDA group III, bufilcon A, lenses with 45% water content) were coated with protein deposits followed by treatment with one of several test solutions (as described in Table I above, except including various amounts of the DeQuest ® 2016 compound). These lenses were then compared with lenses treated with a Control solution consisting of ReNu ® MPS with ReNu ® 1 step enzymatic tablets.

The lenses were treated by means of an in-vitro protein deposit procedure as follows. An aqueous electrolyte solution was prepared, which solution consisted of approximately 0.70% sodium chloride, 0.17% potassium chloride, 0.22 percent sodium bicarbonate, and 0.0005% of calcium chloride, dihydrate. The electrolyte solution was prepared by adding the chlorides and bicarbonate to approximately 90% of the total volume of distilled water required, followed by thorough mixing of the solution. The pH was measured and, if necessary, adjusted to 7.2+/−0.1 with either 1N HCl or 1N NaOH. The solution had osmolality of between 280 to 320. An appropriate amount of the protein lysozyme was then added to the electrolyte solution so that the solution had a 0.10% concentration of lysozyme. The resulting solution was mixed for approximately thirty minutes at moderate speed. The pH was measured (and if necessary, adjusted to 7.2+/−0.1 with either 1N HCl or 1N NaOH). A borate buffered saline solution was also prepared, comprising approximately 0.85% boric acid, 0.09% sodium borate, and 0.45 of sodium chloride. The pH was measured (and if necessary, adjusted to 7.2+/−0.1 with either 1N HCl or 1N NaOH). The osmolality of the solution was between 280 to 320 mOsm/Kg.

Protein deposits were deposited on a number soft hydrogel lenses by placing each lens within a glass vial followed by submerging the lenses in approximately 5 ml of the electrolyte (protein-containing) solution. The vials were then capped and subjected to shaking at 40 rpms in a thermal water bath at approximately 80° C. for about twenty minutes. Subsequently, the lenses were allowed to cool to ambient temperature, followed by gently rubbing the lenses with the borate buffered saline to remove any loosely bound protein.

Once subjected to protein deposits, the lenses were then subjected to treatment with either one of the subject solutions or the Control solution. Treatment with the subject solutions consisted of placing several drops of the test solution on both sides of the lens, followed by rubbing the lens for approximately twenty seconds. The lenses were then rinsed with the test solution and soaked in approximately 5 ml of test solution for four hours. The lenses were then rinsed with a borate buffered saline. Treatment with the Control solution consisted of placing several drops of ReNu ® MPS on both sides of the lens followed by rubbing the lens for approximately twenty seconds. The lenses were then rinsed with fresh ReNu ® MPS and soaked in approximately 10 ml of ReNu ® MPS including one ReNu ® enzyme tablet for approximately four hours. The lenses were subsequently rubbed and rinsed with fresh ReNu ® MPS and finally rinsed with borate buffered saline.

Following the above-described treatment, the lenses were evaluated using microscopic image analysis to determine the amount of protein removed as a result of treatment. The microscopic image analysis consisted of digitally photographing the lenses and analyzing surface debris by gray scale image analysis. This procedure involved placing each lens under a microscope having a "dark field" background and subsequently passing incident light through the lens. Surface debris on the lens scatters light and appears lighter than the clean surface on the contact lens. A digital image of the illuminated lens is obtained and the pixels are counted/separated based on their light intensities using NIH Image V. 1.46 software (National Institute of Health). The values of 90824 pixels in a circular pattern covering the lens were quantified using a scale of 0–255 levels of gray. A value of 0 was defined as "white" while a value of 255 was defined as "black." (Because deposits scatter light, a lighter value indicates a less clean surface.) The mean of these values (mean density) was recorded before and after treatment for each group which consisted of 10 lenses. A percentage difference before and after was then calculated. The higher the percentage change in pixel density, the better the protein removal. The density value of the lenses treated with the test solution was compared with that of lenses treated with the Positive Control solution. From this data, the relative protein removal for each lens was determined. The results of this evaluation are provided in Table II, in which the relative protein removal is indicated in Table II as a percent change in pixel density compared with the Control solution.

TABLE II

| Example No. | % Change in Pixel Density Relative to Control (Control = 100%) |
|---|---|
| 1 (0.01% DeQuest ® 2016) | 82% |
| 2 (0.01% DeQuest ® 2016) | 59% |
| 3 (0.01% DeQuest ® 2016) | 0.0% |
| 4 (0.05% DeQuest ® 2016) | 83% |
| 5 (0.05% DeQuest ® 2016) | 76% |
| 6 (0.10% DeQuest ® 2016) | 76% |
| 7 (0.10% DeQuest ® 2016) | 91% |
| 8 (0.10% DeQuest ® 2016) | 133% |
| 9 (0.25% DeQuest ® 2016) | 79% |
| 10 (0.25% DeQuest ® 2016) | 167% |

Each example is based upon data collected from ten lenses treated in identical manner. As is shown by the data provided in Table II, taking the average for each concentration, the subject solutions and methods for treating lenses provided comparable protein removal to that of the Control solution (which including the use of enzymatic cleaning), although there is reduced activity at lower concentrations. In addition to providing excellent cleaning, the subject solution also provided comparable disinfection as the Control solution.

EXAMPLE 3

This example further illustrates the subject invention, by testing additional phosphonic acid compounds for preventing or removing protein deposits from lenses. Using the in-vitro protein deposit procedure described above in Example 2, soft hydrogel lenses (FDA group III, bufilcon A) were subjected to protein deposits followed by treatment with various test solutions similar to the solution described in Table I above, except including various phosphonic acid compounds in various amounts. Once subjected to protein deposits, the lenses were subjected to treatment with either one of the subject solutions or the Positive Control (Comparative) solution, again consisting of ReNu ® MPS with ReNu ® 1 step enzymatic tablets comprising subtilisin, sodium carbonate, sodium chloride, and boric acid. Following such treatment, the lenses were evaluated using microscopic image analysis to determine the amount of protein removed as a result of treatment. As described above, the microscopic image analysis consisted of digitally photographing the lenses and analyzing surface debris by gray scale image analysis in which each lens is placed under a microscope having a "dark field" background and lincident light is passed through the lens. A digital image of the illuminated lens was obtained and the pixels were counted/separated based on their light intensities. The density value of the lenses treated with a test solution was compared with that of lenses treated with the Positive Control solution. From this data, the relative protein removal for each lens was determined. The results of this evaluation are provided in Table III, which shows the percent change in pixel density. The Table shows (1) the percent change in pixel density employing a subject solution containing a given phosphonic acid compound, (2) the percent change in pixel density employing a comparative enzymatic solution, and, in the last column, (3) the relative percent change in pixel density comparing (1) to (2). The compounds in Table III showed protein-removal activity by a test result meeting at least one of two criteria: (1) showing a relative percent change of about 80 percent or greater, and/or (2) showing a percent change with the compound of greater than 15 percent The average value of percent change for the negative control (ReNu( MPS solution) was about 15 percent.

TABLE III

| Test No. | Phosphonic Compound* | Wt. % (w/v) Compound | % Change with Compound | % Change with Enzyme | Relative % Change Compound To Control |
|---|---|---|---|---|---|
| 1 | 1-hydroxyethylidine-1,1-diphosphonic acid, tetraNa salt | 0.075 | 10 | 6 | 167 |
| 2 | Methylenediphosphonic acid triNa salt, tetrahyd. | 0.10 | 10 | 6 | 167 |
| 3 | 2-Methylbenzylphosphonic acid | 0.10 | 27 | 18 | 150 |
| 4 | 1-hydroxyethylidine-1,1-diphosphonic acid, tetraNa salt | 0.030 | 8 | 6 | 133 |
| 5 | Methylenediphosphonic acid triNa salt, tetrahyd. | 0.01 | 8 | 6 | 133 |
| 6 | 2-aminoethylphosphonic acid | 0.10 | 23 | 19 | 121 |
| 7 | 2-aminoethylphosphonic acid | 0.01 | 23 | 19 | 121 |
| 8 | 2-Methylbenzylphosphonic acid | 1.10 | 53 | 58 | 91 |
| 9 | 1-hydroxyethylidine-1,1-diphosphonic acid, tetraNa salt | 0.030 | 30 | 33 | 91 |
| 10 | 1-hydroxyethylidine-1,1-diphosphonic acid, tetraNa salt | 0.015 | 5 | 6 | 83 |
| 11 | 1-hydroxyethylidine-1,1-diphosphonic acid, tetraNa salt | 0.003 | 27 | 33 | 82 |
| 12 | Aminomethanephosphonic acid | 0.10 | 26 | 32 | 81 |
| 13 | (4-Aminobenzyl) phosphonic acid | 0.10 | 26 | 39 | 67 |
| 14 | Phosphonoacetic acid | 0.01 | 24 | 37 | 65 |
| 15 | DL-2-Amino-4-phosphonobutyric acid | 0.10 | 18 | 28 | 64 |
| 16 | n-Decanephosphonic acid | 0.10 | 20 | 32 | 63 |
| 17 | Phosphonoacetic acid | 0.10 | 23 | 37 | 62 |
| 18 | Benzyl phosphonic acid | 0.10 | 19 | 31 | 61 |
| 19 | 1-hydroxyethylidine-1,1-diphosphonic acid, tetraNa salt | 0.003 | 20 | 34 | 59 |
| 20 | 2-Phosponopropionic acid | 0.10 | 18 | 31 | 58 |
| 21 | 4-Phosphonobutyric acid | 0.10 | 17 | 31 | 55 |
| 22 | hexamethylenediametetra (methylenephosphonic acid), hexapotassium salt | 0.10 | 27 | 53 | 51 |
| 23 | Phosphonoacetic acid | 0.10 | 14 | 28 | 50 |
| 24 | Aminomethanephosphonic acid | 0.10 | 14 | 32 | 44 |
| 25 | 2-Phosphonobutyric acid | 0.10 | 11 | 31 | 35 |
| 26 | diethylenetriaminepenta (methylenephosphonic acid), hexasodium salt | 0.10 | 18 | 53 | 34 |
| 27 | methylene diphosphonic acid | 0.10 | 10 | 31 | 32 |
| 28 | 3-Phosphonopropionic acid | 0.10 | 8 | 28 | 29 |

*All Compounds in Table III are commercially availiable, for example, Compounds 1, 4, 9, 10, 11, and 19 are commercially available from Monsanto Co. (St. Louis); Compounds 2, 5, and 13 are commercially available from Aldrich Co. (Wisconsin); Compounds 3, 5, 12, and 24 are commercially available from Lancaster Co. (Pennsylvania); Compounds 14, 17, and 23 are commercially available from Sigma Chemical Co. (St. Louis); and Compounds 20, 21, 25, 27 and 28 are commercially available from Oakwood Research Chemicals (South Carolina).

As is shown by the data provided in Table III, the subject solutions with phosphonic acid compounds, and methods for treating lenses therewith, provided protein removal better than the Negative Control in at least one test score. Selected or preferred compounds provided protein removal comparable to, or even better than, that of the Positive Control solution that employed an enzymatic cleaning agent.

We claim:

1. A non-oxidative method for treating contact lenses comprising contacting a lens with an ophthalmically safe aqueous solution comprising a phosphonic acid compound, or a physiologically compatible salt thereof, represented by the formula:

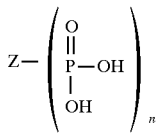

wherein Z is a connecting radical equal in valence to n, wherein n is an integer from 1 to 6, and containing 1 to 12 carbon atoms, and wherein Z is selected from the group consisting of unsubstituted or substituted saturated hydrocarbon radicals and amine-containing radicals, which amine-containing radicals are saturated hydrocarbon radicals in which the carbon atoms are interrupted with at least one nitrogen atom that forms a secondary or tertiary amine and in which the number of carbon atoms in the amine-containing radical is at least n+1, and said substituted saturated hydrocarbon radicals may be substituted with halogen, hydroxy, amine, carboxy, alkylcarbonyl, alkoxycarbonyl and/or substituted or unsubstituted phenyl, and wherein the substituted phenyl may be substituted with halogen, hydroxy, amine, carboxy, alkylcarbonyl, and/or alkyl, and wherein said alkyl or alkoxy groups have 1 to 4 carbon atoms.

2. A non-oxidative method for treating contact lenses according to claim 1 comprising contacting a lens with an ophthalmically safe aqueous solution comprising a phosphonic compound represented by the formula:

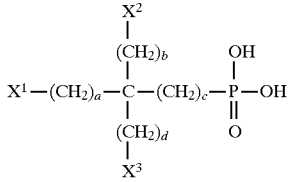

wherein each of a, b, c, and d are independently selected from integers from 0 to 4; $X^1$ is a phosphonic acid, hydroxy, amine or hydrogen group; and $X^2$ and $X^3$ are independently selected from the group consisting of halogen, hydroxy, amine, carboxy, alkylcarbonyl, alkoxycarbonyl, or substituted or unsubstituted phenyl, and methyl, wherein the substituents on the phenyl are one or more halogen, hydroxy, amine, carboxy and/or alkyl groups and wherein said alkyl or alkoxy groups have 1 to 4 carbon atoms.

3. A non-oxidative method for treating contact lenses comprising contacting a lens with an aqueous solution comprising a phosphonic compound represented by the formula:

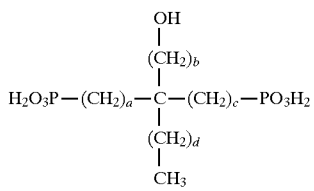

wherein each of a, b, c, and d are independently selected from integers from 0 to 4, and physiologically compatible salts of such phosphonic compounds.

4. The method of claim 1 wherein Z contains 1 to 10 carbon atoms.

5. The method of claim 2 or 3 wherein a, b, c, and d are all 0.

6. The method of claim 1, 2 or 3 wherein the solution further comprises an antimicrobial agent.

7. The method of claim 6 wherein the antimicrobial agent is selected from the group consisting of polymeric biguanides, bis(biguanides), polymeric quaternary ammonium compounds, and salts thereof.

8. The method of claim 1, 2, or 3 wherein the solution has a pH from about 6 to about 8 and an osmolality of between about 250 to 350 mOsm/Kg.

9. The method of claim 1, 2, or 3 comprising the sequential steps of rubbing the lens with the solution, followed by immersing the lens within the solution.

10. An ophthalmically safe non-oxidative aqueous solution having a buffered pH of from about 5 to about 8 and an osmolality of 200 to 450 mOsm/kg for treating contact lenses comprising: a phosphonic compound represented by the formula:

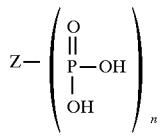

wherein Z is a connecting radical equal in valence to n, wherein n is an integer from 1 to 6, and containing 1 to 12 carbon atoms, and wherein Z is selected from the group consisting of unsubstituted or substituted saturated hydrocarbon radicals and amine-containing radicals, which amine-containing radicals are saturated hydrocarbon radicals in which the carbon atoms are interrupted with at least one nitrogen atom that forms a secondary or tertiary amine and in which the number of carbon atoms in the amine-containing radical is at least n+1, wherein said substituted saturated hydrocarbon radicals may be substituted with halogen, hydroxy, amine, carboxy, alkylcarbonyl, alkoxycarbonyl and/or substituted or unsubstituted phenyl, wherein the substituted phenyl may be substituted with halogen, hydroxy, amine, carboxy and/or alkyl, and wherein said alkyl or alkoxy has 1 to 4 carbon atoms, and an effective amount of at least one non-oxidative antimicrobial agent for a contact-lens treating solution.

11. A non-oxidative aqueous solution according to claim 10 having a pH from about 6 to about 8 for treating contact lenses comprising: a phosphonic compound represented by the formula:

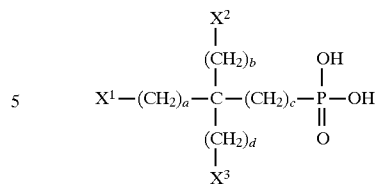

wherein each of a, b, c, and d are independently selected from integers from 0 to 4; $X^1$ is a phosphonic acid, hydroxy, amine or hydrogen group; and $X^2$ and $X^3$ are independently selected from the group consisting of halogen, hydroxy, amine, carboxy, alkylcarbonyl, alkoxycarbonyl, or substituted or unsubstituted phenyl, and methyl, wherein the substituents on the phenyl are one or more halogen, hydroxy, amine, carboxy and/or alkyl groups and wherein said alkyl or alkoxy groups have 1 to 4 carbon atoms.

12. A non-oxidative aqueous solution for treating contact lenses comprising: a phosphonic compound represented by the formula:

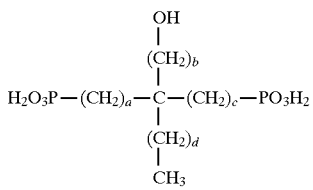

wherein each of a, b, c, and d are independently selected from integers from 0 to 4, and physiologically compatible salts of said phosphonic compounds and further comprising a disinfecting amount of a bactericide selected from the group consisting of biguanides and polymeric quaternary ammonium and salts thereof.

13. The solution of claim 11 or 12 wherein a, b, c, and d are all 0.

14. The solution of claim 10, 11, or 12 wherein the concentration of said phosphonic compound is at least 0.003 percent weight by volume.

15. The solution of claim 10 or 11 wherein the antimicrobial agent is a biguanide or a polymeric quaternary ammonium salt.

16. A non-oxidative method for cleaning and disinfecting a contact lenses with a multi-purpose solution comprising (a) contacting a contact lens with an ophthalmically safe solution comprising about 0.005 to 1.0 percent weight by volume of at least one phosphonic acid compound, or a physiologically compatible salt thereof, wherein the compound has at least one phosphonic acid group and 1 to 12 carbon atoms; and (b) placing the treated contact lens in the eyes of the wearer.

17. A method of disinfecting or cleaning and disinfecting a soft contact lens with a multi-purpose solution, which method comprises:

(a) soaking the lens in an ophthalmically safe solution, such that disinfection of the contact lens is obtained within a minimum recommended soaking period, the solution comprising, in formulation, the following components:

(i) 0.005 to 1.0 percent weight by volume of at least one phosphonic acid compound, or its physiologically compatible salt, which compound has at least one phosphonic acid group and 1 to 12 carbon atoms;

(ii) an effective amount of a surfactant, (iii) an effective amount of a non-oxidative germicide, and (iv) an effective amount of buffering and tonicity agents, and (b) directly placing the treated lens on the eye of the wearer, such that (ii) rinsing with a different solution prior to placement on the eye is not required, and (iii) no other solution is required for daily cleaning of the lens.

18. The method of claim 16 or 17 wherein the solution is used to clean a lens that is made from a polymer comprising about 0.0 to 5 mole percent repeat units derived from methacrylic acid (MAA), 10 to 99 mole percent of repeat units derived from hydroxyethyl methacrylate, and about 0.5 to 5 mole percent of cross-linking repeat units and wherein the lens is planned or set for replacement after not more than about 14 days of wear.

19. The method of claim 16 or 17 wherein the method provides complete cleaning of the lens such that enzymatic cleaning of the lens can be obviated.

20. The method of claim 16 or 17 wherein the phosphonic acid compound contains one or more hydroxyl and/or amine groups.

* * * * *